United States Patent [19]
Randolph

[11] Patent Number: 5,689,030
[45] Date of Patent: Nov. 18, 1997

[54] METHOD FOR PROLONGING THE LIFE OF ALKYLATION PRODUCT STREAM DEFLUORINATOR BEDS

[75] Inventor: Bruce B. Randolph, Bartlesville, Okla.

[73] Assignee: Phillips Petroleum Company, Bartlesville, Okla.

[21] Appl. No.: 611,588

[22] Filed: Mar. 6, 1996

[51] Int. Cl.$^6$ ................................................. C10C 2/62
[52] U.S. Cl. ...................... 585/724; 585/721; 585/723; 585/731; 585/800
[58] Field of Search ........................... 585/723, 724, 585/721, 800

[56] References Cited

U.S. PATENT DOCUMENTS

| | | | |
|---|---|---|---|
| 3,795,712 | 3/1974 | Torck et al. | 260/671 C |
| 4,058,575 | 11/1977 | Cahn et al. | 260/666 P |
| 4,069,268 | 1/1978 | Siskin et al. | 260/666 P |
| 4,118,433 | 10/1978 | Innes | 260/683.51 |
| 4,673,769 | 6/1987 | Farcasiu | 585/458 |
| 5,276,243 | 1/1994 | Better et al. | 585/724 |
| 5,306,859 | 4/1994 | Eastman | 585/724 |
| 5,347,065 | 9/1994 | Anderson | 585/724 |
| 5,347,067 | 9/1994 | Eastman | 585/724 |
| 5,414,186 | 5/1995 | Child et al. | 585/724 |
| 5,461,183 | 10/1995 | Del Rossie et al. | 585/724 |
| 5,569,807 | 10/1996 | Abbott et al. | 585/723 |

*Primary Examiner*—Helane Myers
*Attorney, Agent, or Firm*—Charles W. Stewart

[57] ABSTRACT

A method for prolonging the life of a defluorinator material contained within an alkylation process product stream defluorination zone used to remove organic fluorides from a product stream produced by an alkylation process that utilizes an alkylation catalyst containing HF and sulfone. The life of the defluorinator material is extended by reducing the amount of organic fluorides produced in the alkylation process through the addition of trifluoromethanesulfonic acid to the HF/sulfone alkylation catalyst.

5 Claims, No Drawings

METHOD FOR PROLONGING THE LIFE OF ALKYLATION PRODUCT STREAM DEFLUORINATOR BEDS

The present invention relates to a method for prolonging the life of material used to remove organic fluorides from product streams produced by an alkylation process utilizing a hydrogen fluoride and sulfone catalyst mixture.

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling the mixture to separate the catalyst from the hydrocarbons, and further separating the alkylation reactor effluent, for example, by fractionation, to recover the separate product streams. Normally, the alkylate product of the alkylation process contains hydrocarbons having five to ten carbon atoms per molecule, preferably seven to nine carbon atoms per molecule. In order to have the highest quality gasoline blending stock, it is preferred for the alkylate hydrocarbons formed in the alkylation process to be highly branched and contain seven to nine carbon atoms per molecule.

Recent efforts to improve conventional hydrogen fluoride catalyzed alkylation processes have resulted in the development of new catalyst compositions that contain hydrogen fluoride (also referred to herein as "HF") and a sulfone compound. These new catalyst compositions have been found to be quite effective as an alkylation catalyst and to provide many other favorable benefits. However, it has also been found that in the alkylation process that uses the catalyst mixture of hydrogen fluoride and sulfone there is an increase in the production of undesirable organic fluorides. In fact, as the concentration of hydrogen fluoride in the new catalyst composition becomes more dilute, the amount of organic fluorides produced in the alkylation process increases.

In many instances, it is not desirable for the product streams to have an excessively high concentration of organic fluorides. Thus, the alkylation reactor effluent having a concentration of organic fluorides may be separated, and the individual product streams, such as alkylate, n-butane and propane contacted with a defluorinator material used to remove organic fluorides from such product streams. The rate of defluorinator material consumption is related to the amount of organic fluorides removed from a product stream. Generally, a defluorinator material is more rapidly consumed as the amount of organic fluorides removed from a product stream increases; thus, it is more costly to treat a product stream having a high concentration of organic fluorides than one with a low concentration of organic fluorides.

It is, therefore, an object of this invention to provide a method for prolonging the life of a defluorinator material used to remove organic fluorides from a product stream produced from an alkylation process which uses a catalyst composition comprising hydrogen fluoride and sulfone.

Other objects and advantages of the invention will be apparent from the detailed description of the invention and the appended claims.

Thus, the novel inventive method provides for prolonging the life of a defluorinator material used to remove organic fluoride compounds contained in a product stream of an alkylation process for alkylating olefins by isoparaffins utilizing an alkylation catalyst containing hydrogen fluoride and sulfone. This method includes adding trifluoromethanesulfonic acid (also referred to herein as "TFA") to the alkylation catalyst in an amount sufficient to inhibit the formation of organic fluorides during the alkylation of olefins by isoparaffins in the alkylation process thereby producing product streams having concentrations of organic fluoride less than about 0.5 weight percent. The alkylation reactor effluent is separated and the individual product streams are contacted with a defluorinator material to produce defluorinated product stream having less than 5 ppm organic fluoride.

The alkylation catalyst used in the alkylation process of the present inventive method contains a hydrogen fluoride component and a sulfone component. The hydrogen fluoride of the catalyst composition is preferably in the anhydrous form, but, generally, the hydrogen fluoride component utilized can have a small amount of water. However, the amount of water present in the catalyst composition in no event can be more than about 30 weight percent of the total weight of the hydrogen fluoride. It is preferred for the amount of water present in the hydrogen fluoride component to be less than about 10 weight percent. Most preferably, the amount of water present in the hydrogen fluoride component is less than 5 weight percent. When referring herein to the hydrogen fluoride component of the catalyst composition, it should be understood that this term means either the hydrogen fluoride as an anhydrous mixture or a mixture that includes water. The references herein to weight percent water contained in the hydrogen fluoride means the ratio of the weight of water to the sum weight of the water and hydrogen fluoride multiplied by a factor of 100 to place the weight ratio in terms of percent.

The sulfones suitable for use in this invention are the sulfones of the general formula

wherein R and R' are monovalent hydrocarbon alkyl or aryl substituents, each containing from 1 to 8 carbon atoms. Examples of such substituents include dimethylsulfone, di-n-propylsulfone, diphenylsulfone, ethylmethylsulfone and alicyclic sulfones wherein the $SO_2$ group is bonded to a hydrocarbon ring. In such a case, R and R' are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures.

Typically, the weight ratio of hydrogen fluoride to sulfone in the alkylation catalyst is in the range of from about 39:1 to 1:1. The preferred weight ratio of hydrogen fluoride to sulfone is in the range of from about 19:1 to about 1:1 and, most preferably, the weight ratio is in the range of from 9:1 to 3:1.

While the use of a sulfone as a diluent for a hydrogen fluoride alkylation catalyst provides many valuable advantages, it also causes the increased formation of undesirable organic fluorides during an alkylation reaction in which the alkylation catalyst mixture of hydrogen fluoride and sulfone is utilized as the alkylation catalyst. In fact, as the weight ratio of hydrogen fluoride to sulfone decreases, the amount of organic fluorides produced during alkylation increases.

The production of organic fluorides in the alkylation reaction is undesirable for a number of reasons. Relevant to the instant invention, it is the impact that a high concentration of organic fluorides in a product stream has on the rate at which a defluorinator material becomes spent when treating such organic fluoride-containing product stream.

Since organic fluoride compounds are soluble in the product stream, the increased production of organic fluorides that results from utilizing the hydrogen fluoride and sulfone alkylation catalyst can increase the concentration of organic fluorides in the product streams from the alkylation process thus resulting in a shortened life of defluorinator material used for treating such organic fluoride containing product streams.

Alkylation processes contemplated in the present invention are those liquid phase processes wherein mono-olefin hydrocarbons such as propylene, butylenes, pentylenes, hexylenes, heptylenes, octylenes and the like are alkylated by isoparaffin hydrocarbons such as isobutane, isopentane, isohexane, isoheptane, isooctane and the like for production of high octane alkylate hydrocarbons boiling in the gasoline range and which are suitable for use in gasoline motor fuel. Preferably, isobutane is selected as the isoparaffin reactant and the olefin reactant is selected from propylene, butylenes, pentylenes and mixtures thereof for production of an alkylate hydrocarbon product comprised of a major portion of highly branched, high octane value aliphatic hydrocarbons having at least seven carbon atoms and less than ten carbon atoms.

In order to improve selectivity of the alkylation reaction toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5:1 to about 20:1; and, most preferably, it shall range from 8:1 to 15:1. It is emphasized, however, that the above recited ranges fro the molar ratio of isoparaffin-to-olefin are those which have been found to be commercially practical operating ranges; but, generally, the greater the isoparaffin-to-olefin ratio in an alkylation reaction, the better the resultant alkylate quality.

Isoparaffin and olefin reactant hydrocarbons normally employed in commercial alkylation processes are derived from refinery process streams and usually contain small amounts of impurities such as normal butane, propane, ethane and the like. Such impurities are undesirable in large concentrations as they dilute reactants in the reaction zone, thus decreasing reactor capacity available for the desired reactants and interfering with good contact of isoparaffin with olefin reactants. Additionally, in continuous alkylation processes wherein excess isoparaffin hydrocarbon is recovered from an alkylation reaction effluent and recycled for contact with additional olefin hydrocarbon organic fluorides can also build up in the recycle isobutane stream thereby depressing the purity of the recycle isobutane stream and ultimately reducing the alkylate quality. The nonreactive normal paraffin impurities tend to accumulate in the alkylation system and consequently, process charge streams and/or recycle streams which contain substantial amounts of normal paraffin impurities are usually fractionated to remove such impurities and to maintain their concentration at a low level, preferably less than about 5 volume percent, in the alkylation process. It is in these streams, especially the n-butane exit stream, where organic fluorides are concentrated, the n-butane must be defluorinated before it can be used as a motor fuel component or sold for other uses.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 100° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide for essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40–90 volume percent catalyst phase and about 60–10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

The process may be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalysts.

The continuous operations, in one embodiment, reactants may be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. If desired, a portion of the catalyst can be continuously regenerated or reactivated by any suitable treatment and returned to the alkylation reactor.

A product stream from the alkylation process which uses the alkylation catalyst containing HF and sulfone will generally have a concentration of organic fluorides that is greater than such concentration in a product stream of an alkylation process which uses an alkylation catalyst not containing sulfone. This is due to the greater amounts of organic fluorides produced with the HF/sulfone catalyst. It has been discovered that the addition of trifluoromethanesulfonic acid (TFA) to the alkylation catalyst containing HF and sulfone can be effective in inhibiting the formation of unwanted organic fluorides during the alkylation reaction thereby resulting in a reduction of the organic fluorides concentration in the product streams. The inhibition of organic fluoride formation will also provide for a reduction in the rate at which a fixed quantity of defluorinator material spends because of the reduced quantity of organic fluorides that must be converted by such defluorinator material when the alkylate product is treated. Thus, it is desirable to add TFA to the HF/sulfone alkylation catalyst at an optimum concentration such that the organic fluoride concentration in the product stream is minimized prior to contacting it with a defluorinator material.

The desired concentration of TFA in the alkylation catalyst containing HF and sulfone is in the range of from about 0.5 weight percent to about 10 weight percent of the alkylation catalyst. Preferably, the TFA concentration is in the range of from about 2 weight percent to about 8 weight percent, most preferably, from 3 weight percent to 6 weight percent.

The utilization of the TFA in the alkylation catalyst containing HF and sulfone will reduce the production of organic fluorides thereby resulting in a lower organic fluoride concentration in the product streams from the alkylation process. Thus, the organic fluoride concentration in the product streams can be less than about 0.5 weight percent of the total product stream. Because of the solubility of organic fluorides in hydrocarbon, there will generally be a concentration of organic fluorides usually at least about 10 parts per million by weight (also referred to herein as "ppm"); thus, the concentration range of organic fluorides in a product stream will generally be in the range of from about 10 ppm to about 0.5 weight percent of the product stream. Preferably, the range of organic fluoride concentration in the product stream is from about 10 ppm to about 0.4 weight percent, most preferably, the concentration range is from 10 ppm to 0.3 weight percent.

A product stream from the alkylation process is contacted with a defluorinator material that is suitable for the removal of a substantial portion of the organic fluorides contained in the product stream to produce a defluorinated product stream. This defluorinated product stream shall have a concentration of organic fluorides of less than about 5 ppm. Preferably, the organic fluoride concentration in the defluorinated product stream is less than about 3 ppm, most preferably, less than 1 ppm.

Any suitable defluorinator material may be used which provides for the substantial removal of organic fluorides from an organic fluoride-containing product stream. The preferred defluorinator material is alma. It is believed that the mechanism by which the alumina works to remove organic fluorides from the product stream is by thermal de-hydrofluorination to give HF and an olefin, and reaction of alumina with the thus-produced HF to give aluminum fluoride ($AlF_3$).

The defluorinator material is preferably contained within a conventional vessel, which defines a separation and/or contacting zone for contacting the product stream with the defluorinator material. The reduction in the production of the organic fluorides by use of the TFA additive provides economic benefits by reducing the rate at which the defluorinator material becomes spent and the frequency at which the defluorinator material is replaced.

The contacting or defluorination step is conducted at temperatures in the range of from about 50° F. to about 500° F. and a pressure from atmospheric to about 500 psia.

The following examples are provided to demonstrate the advantages of the present invention. These examples are provided for illustration purposes only and are not intended to limit the invention as set out in the appended claims.

EXAMPLE I

This Example I describes the experimental method used to test the effect of utilizing TFA in an alkylation process that uses an alkylation catalyst containing HF and sulfolane.

A reactor was constructed to enable the steady-state evaluation of HF/sulfolane catalysts with and without TFA. The reactor was a 2'×1" section of monel schedule 40 pipe connected at one end to a monel sight gauge via ¼" monel tubing, and connected at the other end to a feed introduction nozzle via ⅛" monel tubing.

The acid catalyst was blended by addition of HF to a tared sample cylinder containing the desired amounts of water, sulfolane, and TFA. Approximately 300 mL of catalyst mixture was used in each run.

A 9/1 by weight mixture of isobutane/2-butenes feed was blended into a feed cylinder. The feed was pumped through the feed nozzle into the reactor at a rate of 300 mL/hour. The reactor effluent flowed into the monel sight gauge, whereupon the hydrocarbon and any acid carryover were separated.

The hydrocarbon product was drawn off into a suitable sample cylinder, passed over alumina at ambient temperature (to adsorb free HF), collected, and analyzed by standard gas chromatography using a GC sample injection valve so that no light materials were lost. Samples were collected every 1–2 hours, and each experiment was 13 hours in length. The average results for these experiments are given in Table I.

EXAMPLE II

The data presented in Table I were obtained by using the experimental method described in Example I. The data demonstrate the effect of TFA on the performance of an HF/sulfolane alkylation catalyst. As can be seen, the catalyst containing 5 percent TFA provides for as much as 80 percent less organic fluoride production than the HF/sulfolane catalyst not containing TFA. This translates directly to cost savings of as much as or greater than 80 percent with TFA-containing catalysts. Other benefits observed include a reduction in the undesirable cracked products and heavier hydrocarbons. The reduced production of organic fluorides results in a reduction in the amount of organic fluorides that must be removed from a product stream by a defluorinator material.

TABLE I

Effect of TFA on Catalyst Performance

| Products of Alkylation (%) | Catalyst System | | |
| --- | --- | --- | --- |
| | 50/50 HF/Sulfolane | 55/44/1 HF/Sulfolane/Water | 50/45/5 HF/Sulfolane/TFA |
| Avg. Organic Fluoride | 1.54 | 1.87 | 0.26 |
| Avg. iC5–C7 | 14.3 | 15.3 | 8.08 |
| Avg. C9+ | 21.1 | 17.3 | 7.23 |
| Avg. Temp, °F. | 107.3 | 109.4 | 108.0 |

EXAMPLE III

This example is an illustrative case for a commercial-scale facility.

Table II gives the feed flow rates for a typical commercial-scale unit. The feed analysis shows 6.28% n-butane, a portion of which must be purged from the system via fractionation. The fraction to be purged in this example is 0.67 in order to make a 7.0 RVP alkylate. The purged n-butane must be free of organic fluorides before it may be used as a motor fuel component or as a feed for further downstream processing. As is apparent in Table II, the production of organic fluorides in the absence of TFA can be as much as 35–45% of the total n-butane purge stream which would have to be removed during normal operations in order to meet the desired alkylate RVP. The addition of TFA reduces this to approximately 6% of the total n-butane discharge stream, which would drastically lengthen the lifetime of the defluorinator beds.

TABLE II

Calculated Organic Fluoride Production

| | |
|---|---|
| Total Feed Rate | 152,342 lbs/hr |
| n-Butane in Feed | 6.28% by weight |
| Total n-butane charge rate | 9,567 lbs/hr |
| Total n-butane purge rate | 6,410 lbs/hr |
| C4F Production at 1.54% in product | 2,345 lbs/hr |
| % C4F in n-C4 purge stream | 36.6% by weight |
| C4F Production at 1.87% in product | 2,488 lbs/hr |
| % C4F in n-C4 purge stream | 44.4% by weight |
| C4F Production at 0.26% in product | 396 lbs/hr |
| % C4F in n-C4 purge stream | 6.2% by weight |

C4F = Organic Fluorides

While this invention has been described in terms of the presently preferred embodiment, reasonable variations and modifications are possible by those skilled in the art. Such variations and modifications are within the scope of the described invention and the appended claims.

That which is claimed:

1. A method for prolonging the life of a defluorinator material used to remove organic fluoride compounds from a product stream of an alkylation process for alkylating olefins by isoparaffins utilizing an alkylation catalyst containing HF and sulfone, said method comprises the steps of:

adding trifluoromethanesulfonic acid (TFA) to said alkylation catalyst in an amount sufficient to inhibit the formation of organic fluorides during the alkylation of olefins by isoparaffins in said alkylation process;

producing said product stream having a concentration of organic fluoride in the range of from about 10 ppm to about 0.5 weight percent; and contacting said product stream with said defluorinator material to produce a defluorinated product stream having less than 5 ppm organic fluoride.

2. A method as recited in claim 1, wherein said defluorinator material is alumina.

3. A method as recited in claim 2, wherein the amount of TFA added to said alkylation catalyst is such as to provide a concentration of TFA in said alkylation catalyst in the range of from about 0.5 weight percent to about 10 weight percent.

4. A method as recited in claim 3, wherein said concentration of organic fluoride in said product stream is from about 10 ppm to about 0.4 weight percent.

5. A method as recited in claim 4, wherein said concentration of TFA in said alkylation catalyst is from 3 weight percent to 6 weight percent, said concentration of organic fluoride in said product stream is in the range of from 10 ppm to 0.3 weight percent, and said defluorinated product stream has less than 1 ppm organic fluoride.

* * * * *